United States Patent [19]

Hansen et al.

[11] 4,439,622

[45] Mar. 27, 1984

[54] PROCESS OF FORMING LARGE CRYSTALLED 1,3,5-TRIAMINOTRINITROBENZENE

[75] Inventors: Rolf Hansen; Walter Engel, both of Pfinztal; Hiltmar Schubert, Walzbachtal, all of Fed. Rep. of Germany

[73] Assignee: Fraunhofer-Gesellschaft Zur Forderung Der Angewandten Forschung e. V., Munich, Fed. Rep. of Germany

[21] Appl. No.: 340,364

[22] Filed: Jan. 18, 1982

[30] Foreign Application Priority Data

Jan. 21, 1981 [DE] Fed. Rep. of Germany ....... 3101783

[51] Int. Cl.$^3$ ............................................. C07C 85/00
[52] U.S. Cl. .................................................. 564/406
[58] Field of Search ........................................ 564/406

[56] References Cited

U.S. PATENT DOCUMENTS 3,985,595  10/1976  Benziger .................... 564/406 UX
4,032,377   6/1977  Benziger ........................ 564/406

OTHER PUBLICATIONS

Becker, H. J. et al., "Amides Hexavalentes de L'Hexaminobenzene" Oct. 30, 1937.

Primary Examiner—Paul F. Shaver
Attorney, Agent, or Firm—Sandler & Greenblum

[57] ABSTRACT

A process for the manufacture of 1,3,5-triaminotrinitrobenzene having a large crystal size by aminating 1,3,5-trichlorotrinitrobenzene with an agent at atmospheric pressure at a temperature of at least about 160° C. with an antioxidant added to the reaction mixture.

8 Claims, 4 Drawing Figures

PROCESS OF FORMING LARGE CRYSTALLED 1,3,5-TRIAMINOTRINITROBENZENE

BACKGROUND OF THE INVENTION

1. Field of the Invention

The invention relates to a process for the manufacture of large crystalled 1,3,5-triaminotrinitrobenzene (TATB) by amination, e.g., by means of $NH_3$, from 1,3,5-trichloro-2,4,6-trinitrobenzene (TCTNB) at an elevated temperature.

2. Description of Prior Art

Recently, triaminonitrobenzene has been in particular demand as a special explosive. The reason for this is its extraordinary resistance to shock (insensitivity), its high density and its accelerated detonation with respect to classical TNT explosive. More widespread acceptance of this particular explosive has been hindered by the enormously elevated manufacturing costs involved which are many times greater than with conventional explosives.

In the manufacture of TATB one generally starts with trichlorotrinitrobenzene (TCTNB) since this starting material, contrary, for example, to tribromotrinitrobenzene is relatively inexpensive. In a known process (Rev. trav. chim. 56 [1937] 1175) the amination of TCTNB is performed by reaction with aqueous ammonia solution in a low boiling solvent such as ethanol or toluene. After a relatively long reaction time a very fine product having an average crystal size of 10 microns is formed. However, it is difficult to work with such a fine product.

When the explosive is to be poured or pressed as is commonly required, it is preferable to have a size distribution of between about 40 to 250 microns. With such a distribution it is possible to achieve the desired viscosity in the pour mixture as well as to reduce the amount of additives which are necessary for pouring or pressing thereby achieving an elevated explosive density.

So as to achieve these objectives, U.S. Pat. No. 4,032,377, the disclosure of which is hereby incorporated by reference, discloses a technique in which the reaction described above is performed at 150° C. However, according to this technique the pressure is adjusted at this temperature such that the reaction occurs at a considerable excess pressure (35–40 psig). In such a technique large crystalled materials are obtained which are more favorable for subsequent processing. However, the advantages of large crystal size achieved according to this technique are obtained at the expense of increased pressure which requires correspondingly larger and more costly apparatus. This further increases the already elevated costs of manufacture.

SUMMARY OF THE INVENTION

It is, therefore, an object of the invention to provide a process for performing the above reaction which can be conducted with conventional apparatus and at relatively short reaction times so as to provide TATB having a large crystal size distribution.

According to the process, 1,3,5-triaminotrinitrobenzene having a large crystal size is formed by aminating 1,3,5-trichlorotrinitrobenzene with an aminating agent having a decomposition temperature above 60° C. at a temperature greater than 160° C. in the presence of an effective amount of at least one antioxidant. Under these conditions the reaction can be conducted at substantially atmospheric pressure.

DESCRIPTION OF PREFERRED EMBODIMENTS

To achieve the above objectives, the invention provides a technique in which the amination occurs at a reaction temperature greater than about 160° C. with the addition of an antioxidant when the temperature of the reaction is about 160° C.

Tests have shown that when the amination reaction is conducted about 160° C., i.e., at a temperature which is in the vicinity of the formation temperature of TATB, a product having a sufficiently large crystal size can be formed without any excess pressure. So as to operate at this higher temperature without risking degradation of the substance, which manifests itself by a continuous darkening of the product, antioxidants, e.g., ethyltriphenylurea, are added in small quantities. As a result of short reaction times and the direct addition of the amination agent and antioxidants it is possible without any further precautions to achieve a reaction which can be controlled and occurs at ambient or atmospheric pressures. By way of example, the amination agents which may be used and which satisfy the above conditions include ammonium acetate, ammonium oxalate, ammonium carbamate, and urea as well as ammonia itself. The reaction which occurs at temperatures greater than 160° C. can be achieved by various techniques:

According to one embodiment, the TCTNB can be melted and the melt mixed with the amination agent in either the solid state, the melted state or the gaseous state. Alternately, the amination agent can be brought to a temperature near its decomposition temperature and the TCTNB can be added in the solid or liquid state.

According to a preferred embodiment the TCTNB is dissolved in a solvent whose boiling point is greater than 160° C. and the solution is brought to a temperature greater than about 160° C. with the amination agent being added.

According to this embodiment the TATB which is formed precipitates together with ammonium chloride while TCTNB remains in solution. The solvent is selected such that it is inert to TCTNB. As a result substantially reduced reaction times are possible. Furthermore, an increase in the average crystal size at the expense of smaller crystal sizes is noted when the TATB is somewhat soluble in the reacton medium. It is surprising that the type of solvent effects the formation temperature of the TATB so that conversely the formation of decomposition products can be controlled by properly selecting the solvent.

As particularly preferred solvents trioctylphosphate, silicon oil, dibutylphthalate, (linear polymeric dimethyl siloxane with a boiling point above 160° C.) Decalin (decahydronaphthalene), nitrobenzene or paraffin oil are selected.

The invention will now be described with particular reference to specific process parameters, given by way of example only, with reference to the microphotographs of FIGS. 1–4 illustrating the crystal sizes.

EXAMPLE 1

Figure 1:
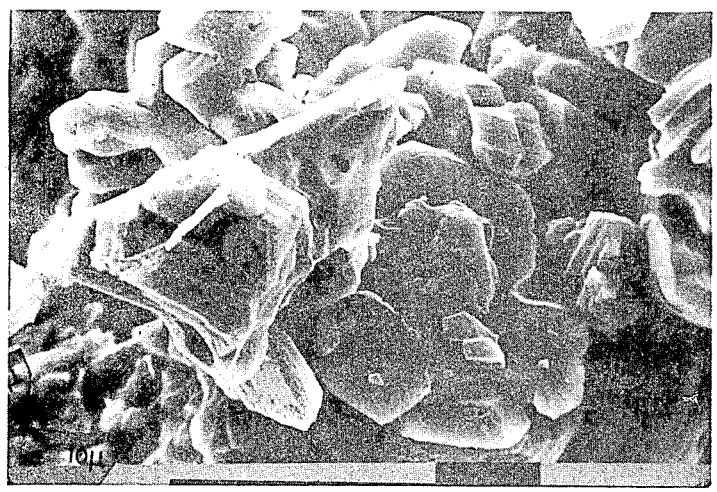
FIG. 1 is a magnified photograph of TATB crystals formed by amination with urea in a TCTNB melt.

A melt containing 0.1 kilograms TCTNB is placed in a heated vessel with 2 grams of ethyltriphenylurea at 190° C. and is quickly mixed with 0.15 kilograms of melted urea. After reaction during three minutes the mixture is quickly cooled and washed with aqueous acetone solution. The product has the following characteristics and is illustrated in FIG. 1:

Yield—75%,
Density—1.93 grams/CM$^3$,
Crystal Size—50 microns,
Chloride Content—Greater than 0.01%,
Decomposition Temp.—361° C.*
*(measured by differential thermal analysis).

EXAMPLE 2

Figure 2:
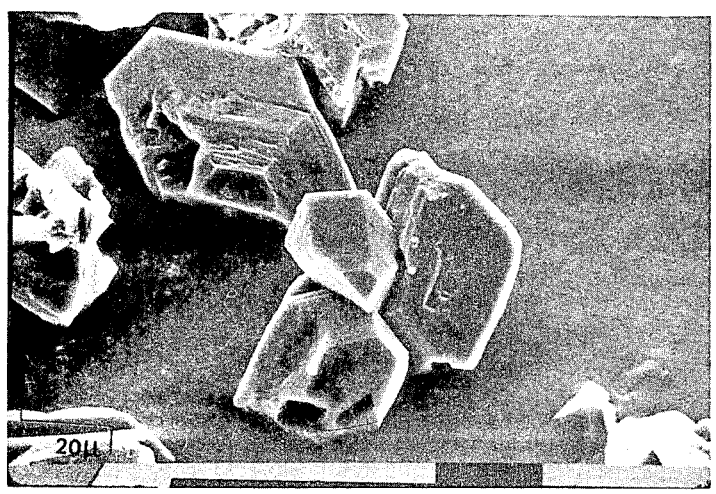
FIG. 2 is a magnified photograph of TATB formed by amination with urea in nitrobenzene.

The amination of TCTNB is performed at a reaction temperature greater than 160° C. in nitrobenzene (or boiling chlorobenzene). 0.5 kilograms of TCTNB, 10 grams of ethyltriphenylurea and 0.75 kilograms of urea are dissolved in 1 kilogram of hot nitrobenzene. Above 150° C. TATB begins to precipitate. As a result of the reaction temperature the process occurs in two hours. The precipitate is washed with acetone and water until substantially no chlorine containing compounds remain. The product has the following characteristics and is illustrated in FIG. 2.

Yield—65%,
Chloride Content—Greater than 0.01%,
Density—1.84 grams/CM$^3$,
Crystal Size—150 microns,
Decomposition Temp.—359° C.*
* (measured by differential thermal anaylsis).

EXAMPLE 3

Figure 3:
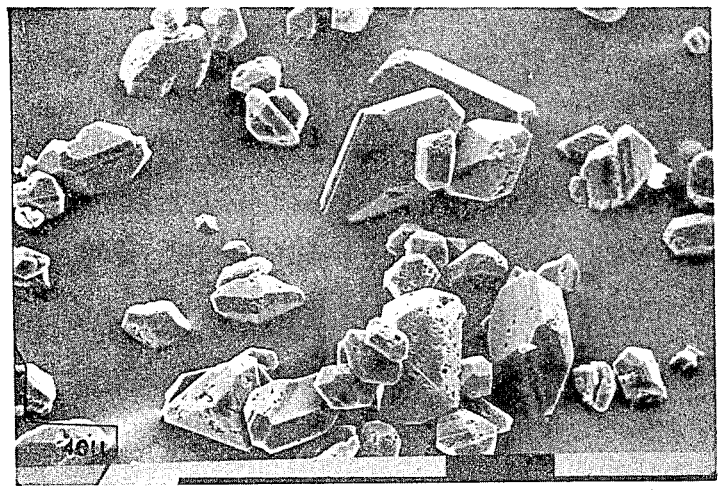
FIG. 3 is a magnified photograph formed by amination with ammonia in boiling chlorobenzene.
Figure 4:
FIG. 4 is a magnified photograph of TATB formed by amination with ammonia in boiling nitrobenzene.

The amination of 0.5 kilograms of TCTNB is performed in one kilogram of hot nitrobenzene or boiling chlorobenzene by addition of gaseous ammonia with further addition of 10 grams of ethyltriphenylurea. As a function of the selected temperature the TATB precipitates out within about two hours. The precipitate is washed with acetone and water until substantially no chlorine-containing compounds remain. The product exhibits the following characteristics and is illustrated in FIGS. 3 and 4.

Yield—55%,
Chloride Content—Greater than 0.01%,
Density—1.90 grams/CM$^3$,
Crystal Size—50–300 microns,
Decomposition Temp.—358° C.*
*(measured by differential thermal analysis).

Although the invention has been described with reference to specific agents and materials it is to be understood that the invention is not limited to the particulars disclosed and extends to all equivalents falling within the scope of the claims.

What is claimed is:

1. A process for the manufacture of 1,3,5-triaminotrinitrobenzene having a large crystal size comprising aminating 1,3,5-trichlorotrinitrobenzene with an aminating agent having a decomposition temperature above 160° C. at a temperature greater than about 160° C. in the presence of an effective amount of at least one antioxidant.

2. The process as defined by claim 1 comprising aminating with an agent selected from the group consisting of ammonium acetate, ammonium oxalate, ammonium carbamate, urea or ammonia.

3. The process as defined by claim 1 wherein said 1,3,5-trichlorotrinitrobenzene is a melt and wherein said agent is a solid, melt or gas added to said melt.

4. The process as defined by claim 1 comprising heating said aminating agent to a temperature above about 160° C. near its decomposition temperature and adding said 1,3,5-trichlorotrinitrobenzene to said aminating agent in the solid or liquid state.

5. The process as defined by claim 1 comprising dissolving said 1,3,5-trichlorotrinitrobenzene in a solvent having a boiling point greater than about 160° C. to form a solution, heating said solution to a temperature greater than about 160° C., and adding said aminating agent to said solution.

6. The process as defined by claim 5 wherein said solvent is trioctylphosphate, silicon oil, dibutylphthalate, Decalin, nitrobenzene or paraffin oil.

7. The process as defined by claim 1 wherein said antioxidant is ethyltriphenylurea.

8. A process for forming crystals having a size distribution between about 40 and 250 microns of 1,3,5-triaminotrinitrobenzene comprising aminating 1,3,5-trichlorotrinitrobenzene at atmospheric pressure at a temperature of at least about 160° C. and adding an antioxidant during amination.

* * * * *

UNITED STATES PATENT AND TRADEMARK OFFICE
CERTIFICATE OF CORRECTION

PATENT NO. : 4,439,622

DATED : March 27, 1984

INVENTOR(S) : Rolf HANSEN et al.

It is certified that error appears in the above-identified patent and that said Letters Patent is hereby corrected as shown below:

In column 2, lines 20 and 22, delete "about" and substitute ---above---

On the face page, in the Other Publications section, delete "Becker" and substitute ---Backer---

Signed and Sealed this

Eighteenth Day of December 1984

[SEAL]

Attest:

GERALD J. MOSSINGHOFF

Attesting Officer     Commissioner of Patents and Trademarks